United States Patent [19]

Hasegawa et al.

[11] 4,435,600

[45] Mar. 6, 1984

[54] PROCESS FOR PREPARATION OF TERTIARY BUTYL HYDRAZINE

[75] Inventors: Yoichi Hasegawa, Marugame; Mineo Nakagawa, Takamatsu; Syuji Hara, Zentsuji, all of Japan

[73] Assignee: Japan Hydrazine Co., Inc., Tokyo, Japan

[21] Appl. No.: 474,000

[22] Filed: Mar. 10, 1983

[51] Int. Cl.$^3$ .......................................... C07C 109/02
[52] U.S. Cl. .................................................... 564/464
[58] Field of Search ........................................ 564/464

[56] References Cited

U.S. PATENT DOCUMENTS 3,072,713  1/1963  Gutmann .................... 564/464 X
3,209,032  9/1965  Helm .......................... 564/464 X
3,313,855  4/1967  Appel .......................... 564/464
4,286,108  8/1981  Osborg ........................ 564/464

Primary Examiner—Paul F. Shaver
Attorney, Agent, or Firm—Sherman & Shalloway

[57] ABSTRACT

Disclosed is a process for the preparation of a tertiary butyl hydrazine hydrohalogenide, which comprises reacting a hydrazine salt of a hydrohalogenic acid with tertiary butanol in the presence of a hydrazine dihydrohalogenide or a hydrogen halide.

Also disclosed is a process for the preparation of tertiary butyl hydrazine, which comprises reacting a hydrazine salt of a hydrohalogenic acid in the presence of a hydrazine dihydrohalogenide or a hydrogen halide, neutralizing the formed tertiary butyl hydrazine hydrohalogenide by an alkali, distilling the neutralization product and recovering free tertiary butyl hydrazine.

8 Claims, No Drawings

PROCESS FOR PREPARATION OF TERTIARY BUTYL HYDRAZINE

BACKGROUND OF THE INVENTION (1) Field of the Invention

The present invention relates to a novel process for the preparation of tertiary butyl hydrazine (hereinafter referred to as "TBH"). More particularly, the present invention relates to a process comprising reacting a hydrazine salt of a hydrohalogenic acid (hereinafter referred to as "H.HX") with tertiary butanol (hereinafter referred to as "t-BuOH") in the presence of a hydrazine dihydrohalogenide (hereinafter referred to as "H.2HX") or a hydrogen halide (hereinafter referred to as "HX") to obtain a tertiary butyl hydrazine hydrohalogenide (hereinafter referred to as "TBH.HX") and, if desired, converting said compound to TBH.

(2) Description of the Prior Art

We previously proposed a process comprising reacting H.HX with a tertiary butyl halide (hereinafter referred to as "t-BuX") to obtain TBH.HX and forming TBH from TBH.HX (see the specification of U.S. Pat. No. 4,310,696). t-BuX is obtained from t-BuOH and HX. For example, tertiary butyl chloride (hereinafter referred to as "t-BuCl") is obtained from t-BuOH and concentrated hydrochloric acid, but in order to advance the reaction quantitatively, concentrated hydrochloric acid containing HCl in an amount at least 3 times as large as the stoichiometric amount should be used. If the HCl concentration is reduced, the reaction is not quantitatively advanced, and unreacted hydrochloric acid having a reduced concentration should be discarded after neutralization. This is a disadvantage involved in the preparation of t-BuCl, which is used in the conventional process for the preparation of TBH.

SUMMARY OF THE INVENTION

Under the above-mentioned background, we made researches with a view to developing a process capable of producing TBH by direct reaction of cheap t-BuOH with H.HX, and as the result, we have now completed the present invention.

We first tried to react hydrazine monohydrochloride (hereinafter referred to as "H.HCl") with t-BuOH in an autoclave, and it was found that this reaction is different from the reaction of H.HCl with t-BuCl and the pressure in the autoclave is drastically elevated, and that the hydrochloride of tertiary butyl hydrazine is not formed by this reaction but isobutylene is formed by dehydration of t-BuOH.

To our great surprise, it was found that if H.HCl is reacted with t-BuOH in the presence of hydrazine dihydrochloride (hereinafter referred to as "H.2HCl") or HCl, tertiary butyl hydrazine hydrochloride (hereinafter referred to as "TBH.HCl") is quantitatively formed. We furthered our researches based on this finding, and we have now completed the present invention.

More specifically, in accordance with one fundamental aspect of the present invention, there is provided a process for the preparation of a tertiary butyl hydrazine hydrohalogenide, which comprises reacting a hydrazine salt of a hydrohalogenic acid with tertiary butanol in the presence of a hydrazine dihydrohalogenide or a hydrogen halide.

In accordance with another aspect of the present invention, there is provided a process for the preparation of tertiary butyl hydrazine, which comprises reacting a hydrazine salt of a hydrohalogenic acid in the presence of a hydrazine dihydrohalogenide or a hydrogen halide, neutralizing the formed tertiary butyl hydrazine hydrohalogenide by an alkali, distilling the neutralization product and recovering free tertiary butyl hydrazine.

According to the present invention, cheap t-BuOH can directly be used as the starting reactant without using t-BuCl, and therefore, equipment for the preparation of t-BuCl is not necessary at all. Furthermore, disposal of waste hydrochloric acid or handling of expensive high-pressure hydrogen chloride gas becomes unnecessary. Moreover, according to the present invention, the reaction can be performed even under atmospheric pressure. Therefore, the present invention is economically advantageous from the viewpoint of either equipment or operation.

DETAILED DESCRIPTION OF THE PREFERRED EMBODIMENTS

The process of the present invention is expressed by the following reaction formula:

$$\text{H.HX} + \text{t-BuOH} \xrightarrow{\text{catalyst (H.2HX or HX)}} \text{TBH.HX} + \text{H}_2\text{O}$$

In carrying out the process of the present invention, it is preferred that the HX/H.HX or H.2HX/H.HX molar ratio be lower than 2, especially 0.1 to 1.25, and the t-BuOH/H.HX molar ratio be lower than 1.5, especially 0.1 to 1.25.

The reaction temperature is 80° to 140° C., preferably 90° to 110° C. Water can be used as the solvent. From the industrial viewpoint, it is preferred that an aqueous solution of H.HX prepared from hydrazine and hydrochloric acid be used. The reaction may be carried out under either elevated pressure or atmospheric pressure, and the reaction can be conducted batchwise or in a continuous manner.

In this reaction, if H.HX is used in an amount excessive over the amount of t-BuOH, unreacted H.HX is left, and even though t-BuOH is used in an amount excessive over the amount of H.HX, a minute amount of H.HX is left. Accordingly, in each case, in order to obtain TBH.HX of a high purity, it is necessary to separate H.HX from TBH.HX. For this purpose, water is used as the solvent and the liquid reaction mixture is recycled to saturate the liquid reaction mixture with TBH.HX, and if the saturated liquid reaction is cooled, high-purity TBH.HX is precipitated in the form of crystals and it can be separated from H.HX. The mother liquor from which TBH.HX has been separated is preferably recycled and used again.

As is apparent from the foregoing description, according to the present invention, reaction of t-BuOH with H.HX is advanced very easily without substantial formation of by-products and TBH.HX can be obtained quantitatively.

According to the present invention, TBH is first obtained in the form of TBH.HX, and it can be used in the form of TBH.HX as the starting material for various synthesis reactions. When recovery of free TBH is desired, neutralization is performed with an alkali such as sodium hydroxide and distillation is then performed, whereby an aqeuous solution of TBH is obtained.

If a strong alkali such as sodium hydroxide is added to this aqueous solution and dehydration distillation is carried out, or if a strong alkali is added to this aqueous solution and the upper layer of TBH is separated from the lower aqueous layer, substantially anhydrous, high-purity TBH can be recovered.

The present invention will now be described in detail with reference to the following Examples that by no means limit the scope of the invention.

Example 1

A 200 ml-capacity four-neck flask equipped with a reflux condenser, a stirrer, a dropping funnel and a thermometer was charged with 137.0 g of a 50% H.HCl aqueous solution (1.0 mole as H.HCl) and 13.0 g of concentrated hydrochloric acid (0.125 mole as HCl), and the mixture was heated at 105° C. and 9.3 g (0.125 mole) of t-BuOH was added dropwise with stirring through the dropping funnel over a period of about 1 hour. After completion of the dropwise addition, the reaction mixture was stirred at the above-mentioned temperature for 30 minutes, and 158.5 g of the obtained liquid reaction mixture was analyzed by gas chromatography. It was found that the content of TBH.HCl was 9.7%, the amount formed of TBH.HCl was 15.4 g and the yield was 99%.

Example 2

A 1 liter-capacity four-neck flask equipped with a reflux condenser, a stirrer, a dropping funnel and a thermometer was charged with 273.8 g (4.0 moles) of H.HCl, 104.3 g of concentrated hydrochloric acid (1.0 mole as HCl) and 643 g of water, and the mixture was heated at 100° to 105° C. with stirring and 74.0 g (1.0 mole) of t-BuOH was added dropwise through the dropping funnel over a period of 4 hours. The reaction mixture was then stirred for 30 minutes and cooled to obtain 1094.0 g of the liquid reaction mixture. The obtained reaction mixture was analyzed by gas chromatography. It was found that the content of TBH.HCl was 11.4%, the amount formed of TBH.HCl was 124.7 g and the yield was 100%.

Example 3

A 500 ml-capacity four-neck flask equipped with a reflux condenser, a stirrer, a dropping funnel and a thermometer was charged with 102.8 g (1.5 moles) of H.HCl, 104.3 g of concentrated hydrochloric acid (1.0 mole as HCl) and 308.4 g of water, and the mixture was heated with stirring and 74.1 g (1.0 mole) of t-BuOH was added dropwise at 100° to 105° C. over a period of 2.5 hours. After completion of the dropwise addition, the reaction mixture was stirred for 30 minutes and cooled, and the obtained liquid reaction mixture (587.6 g) was analyzed by gas chromatography. It was found that the content of TBH.HCl was 20.8%, the amount formed of TBH.HCl was 122.0 g and the yield was 97.9%.

Example 4

A 500 ml-capacity four-neck flask equipped with a reflux condenser, a stirrer, a dropping funnel and a thermometer was charged with 54.8 g (0.8 mole) of H.HCl, 104.3 g of concentrated hydrochloric acid (1 mole as HCl) and 164.4 g of water, and the mixture was heated with stirring and 74.1 g (1.0 mole) of t-BuOH was added dropwise at 82° to 105° C. through the dropping funnel over a period of 4 hours. After completion of the dropwise addition, the reaction mixture was stirred for 30 minutes and then cooled, and 388.6 g of the obtained liquid reaction mixture was analyzed by gas chromatography. It was found that the content of TBH.HCl was 24.9%, the amount formed of TBH.HCl was 96.76 g and the yield was 97.1%.

Example 5

A 300 ml-capacity four-neck flask equipped with a reflux condenser, a dropping funnel, a stirrer and a thermometer was charged with 68.5 g (1 mole) of H.HCl, 20.9 g of concentrated hydrochloric acid (0.2 mole as HCl) and 159.8 g of water, and the mixture was heated with stirring and 37.05 g (0.5 mole) of t-BuOH was added dropwise at 100° to 105° C. over a period of 12 hours. After completion of the dropwise addition, the reaction mixture was stirred for 30 minutes at the above-mentioned temperature and was then cooled, and 284.5 g of the obtained liquid reaction mixture was analyzed by gas chromatography. It was found that the content of TBH.HCl was 21.2%, the amount formed of TBH.HCl was 60.31 g and the yield was 96.8%.

Example 6

A 500 ml-capacity four-neck flask equipped with a relfux condenser, a dropping funnel, a stirrer and a thermometer was charged with 68.5 g (1.0 mole) of H.HCl, 104.3 g of concentrated hydrochloric acid (1.0 mole as HCl) and 159.8 of water, and the mixture was heated with stirring and 37.05 g (0.5 mole) of t-BuOH was added dropwise through the dropping funnel at 102° to 105° C. over a period of 5 hours. After completion of the dropwise addition, the reaction mixture was stirred at the above-mentioned temperature and was then cooled, and 366.4 g of the obtained liquid reaction mixture was analyzed by gas chromatography. It was found that the content of TBH.HCl was 16.8%, the amount formed of TBH.HCl was 61.56 g and the yield was 98.8%.

Example 7

A 500 ml-capacity glass autoclave was charged with 143.7 g (2.1 moles) of H.HCl, 31.5 g (0.3 mole) of H.2HCl, 175.2 g of water and 22.2 g (0.3 mole) of t-BuOH, and the autoclave was sealed and reaction was carried out at 100° C. with stirring for 2 hours. The maximum pressure during the reaction was 3.4 kg/cm$^2$ G. After completion of the reaction, the reaction mixture was cooled, and 370 g of the obtained liquid reaction mixture was taken out and analyzed by gas chromatography. It was found that the content of TBH.HCl was 9.9%, the amount formed of TBH.HCl was 36.63 g and the yield was 98.0%.

Example 8

A 200 ml-capacity four-neck flask equipped with a reflux condenser, a stirrer, a dropping funnel and a thermometer was charged with 137.0 g a 50% H.HCl aqueous solution (1.0 mole as H.HCl) and 13.1 (0.125 mole) of H.2HCl, and the mixture was heated at 105° C. and 9.3 g (0.125 mole) of t-BuOH was added dropwise with stirring through the dropping funnel over a period of about 1 hours. After completion of the dropping funnel, the reaction mixture was stirred at the above-mentioned temperature for 30 minutes, and 158.0 g of the obtained liquid reaction mixture was analyzed by gas chromatography. It was found that the content of TBH.HCl was 9.7%, the amount formed of TBH.HCl was 15.3 g and the yield was 98.4%.

Example 9

A 300 ml-capacity four-neck flask equipped with a reflux condenser, a dropping funnel, a thermometer and a stirrer was charged with 50.1 g (1.0 mole) of 100% hydrazine hydrate and 206.6 g of a 47% aqueous solution of hydrobromic acid (1.2 moles as HBr), and the mixture was heated with stirring and 14.8 g (0.2 mole) of t-BuOH was added dropwise at 100° to 105° C. through the dropping funnel over a period of 3 hours. The reaction mixture was stirred at the above-mentioned temperature and cooled, and 270 g of the obtained liquid reaction mixture was analyzed by gas chromatography. It was found that the content of the HBr salt of TBH was 12.3% by weight, the amount formed of this salt was 33.21 g and the yield of 98.5%.

Example 10

A 1 liter-capacity four-neck flask equipped with a reflux condenser, a dropping funnel, a stirrer and a thermometer was charged with 100 g of a liquid containing 159.9 g (1 mole) of hydrazine monohydroiodide, which obtained by reacting iodine with hydrazine in water, 25.6 g (0.2 mole) of HI and 814.5 g of water, and 14.8 g (0.2 mole) of t-BuOH was added dropwise through the dropping funnel under heating and agitation at 100° to 105° C. over a period of 1.5 hours. After completion of the dropwise addition, the liquid reaction mixture was cooled to room temperature and 1012.8 g of the obtained liquid reaction mixture was analyzed by gas chromatography. It was found that the content of the HI salt of TBH was 1.40% by weight, the amount formed of this salt was 14.18 g and the yield was 32.8%.

Example 11

A 50 liter-capacity glass-lined reaction vessel equipped with a reflux cooler, a thermometer and a stirrer was charged with 9.305 kg (135.8 moles) of H.HCl, 3.129 kg of concentrated hydrochloric acid (30 moles as HCl) and 16.092 kg of water, and the mixture was heated at 100° to 105° C. with steam and 6.743 kg (91 moles) of t-BuOH was supplied over a period of 10 hours by a metering pump to effect reaction. The reaction was further conducted for 30 minutes, and the obtained liquid reaction mixture (35.21 kg) was analyzed by gas chromatography. It was found that the content of TBH.HCl was 31.9%, the amount formed of TBH.HCl was 11.23 kg and the yield was 99.0%.

Example 12

To the liquid reaction mixture obtained in Example 11 were added concentrated hydrochloric acid and H.HCl in a 50 liter-capacity glass-lined reaction vessel, and t-BuOH was supplied by a metering pump. In the same manner as described in Example 11, the reaction was carried out, and the liquid reaction mixture was cooled and the precipitated TBH.HCl crystal was separated and dried. The obtained mother liquid was recycled and the reaction was repeated in the same manner. The obtained results are shown in Table 1. When the mother liquid was thus recycled 7 times, the TBH.HCl crystal having an average purity of 99.26% was obtained in a yield of 97.7%.

TABLE 1

Results of Synthesis of TBH.HCl

| Experiment No. | Mother Liquid Recycled | | | | Concentrated Hydrochloric Acid Added (kg) (mole) | H.HCl (Kg) (mole) | t-BuOH (kg) (mole) | Time for Supply of t-BuOH (hr) | Reaction Temperature (°C.) | TBH.HCl | | |
|---|---|---|---|---|---|---|---|---|---|---|---|---|
| | Total Amount (kg) | TBH.HCl (%) (mole) | H.HCl (%) (mole) | HCl (mole) | | | | | | Amount Obtained (kg) | Purity (%) | Yield (%) |
| 1 | 35.21 | 31.92 90.27 | 8.88 45.64 | 28.44 | 0.50 4.80 | 2.055 30 | 2.22 30 | 1.5 | 100–104 | 3.64 | 99.19 | 96.57 |
| 2 | 35.64 | 34.12 97.51 | 7.88 41.00 | 30.93 | 0 | 30 | 30 | 1.6 | 99–102 | 5.05 | 98.89 | 133.58 |
| 3 | 34.58 | 29.57 82.07 | 7.70 38.87 | 29.85 | 0 | 30 | 30 | 1.75 | 100–101 | 1.41 | 99.89 | 37.67 |
| 4 | 37.11 | 33.33 99.27 | 6.99 37.27 | 29.11 | 0.10 0.959 | 30 | 30 | 1.5 | 102.5 | 2.93 | 99.81 | 78.22 |
| 5 | 38.15 | 38.52 117.94 | 6.71 37.37 | 30.27 | 0 | 30 | 30 | 1.9 | 101–102 | 3.60 | 99.36 | 95.68 |
| 6 | 38.17 | 33.60 102.93 | 6.83 38.06 | 28.99 | 0.10 0.959 | 30 | 30 | 1.3 | 100–104 | 4.77 | 98.76 | 126.01 |
| 7 | 37.26 | 31.54 94.32 | 6.92 37.64 | 28.87 | 0.959 | 30 | 30 | 1.5 | 103–105 | 2.71 | 99.54 | 72.15 |
| 8 | 38.37 | 33.56 103.35 | 6.89 38.59 | 29.34 | After about 3 kg of water was removed by concentration, the remained mixture was cooled, and the crystal was separated and dried. | | | | | 1.64 | 99.78 | — | total amount obtained of TBH.HCl = 25.75 kg, average purity = 99.26%, yield = 97.7%

Example 13

To 100 g of TBH.HCl (purity=99.5%; 0.798 mole) were added 100 g of water and 32.4 g of flaky caustic soda, and the mixture was subjected to simple distillation and 175.8 g of a fraction boiling at 102° to 103° C. was obtained (the TBH content was 39.0% by weight and the recovery ratio was 97.5%).

Example 14

To 778 g of TBH.HCl (purity=96.0%; 6.0 moles) were added 778 g of water and 284 g of flaky caustic soda, and the mixture was subjected to simple distillation to obtain 831 g of a first fraction (the TBH content was 50.7% by weight) and 311 g of a second fraction (the TBH content was 26.6% by weight). Then, 800 g of flaky caustic soda was added to 828 g of the first fraction, and the mixture was rectified in a rectification column (packed with Heli Pack No. 3) having a height of 600 mm and an inner diameter of 20 mm and 266 g of a fraction boiling at 117° to 118° C. was obtained (the TBH purity was 97.7%).

Example 15

To 370 g of an aqueous solution of TBH (the TBH content was 40.6% by weight) was added 222 g (same as the amount of water) of flaky caustic soda, and the mixture was heated at 90° C. and stirred to form a solution. The solution was cooled to cause phase separation, and the upper TBH layer was recovered to obtain 119 g of TBH having a TBH content of 96.2%.

What is claimed is:

1. A process for the preparation of a tertiary butyl hydrazine hydrohalogenide, which comprises reacting a hydrazine salt of a hydrohalogenic acid with tertiary butanol in the presence of a hydrazine dihydrohalogenide or a hydrogen halide.

2. A process according to claim 1, wherein the hydrazine dihydrohalogenide or hydrogen halide is made present in an amount smaller than 2 moles per mole of the hydrazine salt of the hydrohalogenic acid and a molar ratio of tertiary butanol to the hydrazine salt of the hydrohhalogenic acid is lower than 1.5.

3. A process according to claim 1, wherein the hydrazine dihydrohalogenide or hydrogen halide is made present in an amount of 0.1 to 1.25 moles per mole of hydrazine salt of the hydrohalogenic acid and a molar ratio of tertiary butanol to the hydrazine salt of the hydrohalogenic acid is 0.1 to 1.25.

4. A process according to claim 1, wherein the reaction is carried out in an aqueous medium.

5. A process according to claim 1, wherein the reaction is carried out at a temperature of 80° to 140° C.

6. A process for the preparation of tertiary butyl hydrazine, which comprises reacting a hydrazine salt of a hydrohalogenic acid in the presence of a hydrazine dihydrohalogenide or a hydrogen halide, neutralizing the formed tertiary butyl hydrazine hydrohalogenide by an alkali, distilling the neutralization product and recovering free tertiary butyl hydrazine.

7. A process according to claim 6, wherein tertiary butyl hydrazine is recovered in the form of an aqueous solution, a strong alkali is added to the aqueous solution and the solution is separated into a lower aqueous layer and an upper tertiary butyl hydrazine layer.

8. A process according to claim 6, wherein tertiary butyl hydrazine is recovered in the form of an aqueous solution, a strong alkali is added to the recovered aqueous solution and the mixture is rectified to recover substantially anhydrous tertiary butyl hydrazine.

* * * * *

UNITED STATES PATENT AND TRADEMARK OFFICE
CERTIFICATE OF CORRECTION

PATENT NO. : 4,435,600
DATED : March 6, 1984
INVENTOR(S) : Yoichi Hasegawa et al.

It is certified that error appears in the above-identified patent and that said Letters Patent is hereby corrected as shown below:

On the title page insert

-- /30/ Foreign Application Priority Data

January 25, 1983    Japan    58-9445  --.

Signed and Sealed this

Thirty-first Day of July 1984

[SEAL]

*Attest:*

*Attesting Officer*

GERALD J. MOSSINGHOFF

*Commissioner of Patents and Trademarks*